(12) United States Patent
Isolauri et al.

(10) Patent No.: US 7,862,808 B2
(45) Date of Patent: Jan. 4, 2011

US007862808B2

(54) **METHOD FOR PREVENTING OR TREATING RESPIRATORY INFECTIONS AND ACUTE OTITIS MEDIA IN INFANTS USING *LACTOBACILLUS RHAMNOSUS* LGG AND *BIFIDOBACTERIUM LACTIS* BB-12**

(75) Inventors: Erika Isolauri, Nurmijarvi (FI); Seppo Salminen, Turku (FI)

(73) Assignee: Mead Johnson Nutrition Company, Evansville, IN (US)

( * ) Notice: Subject to any disclaimer, the term of this patent is extended or adjusted under 35 U.S.C. 154(b) by 393 days.

(21) Appl. No.: 11/170,405

(22) Filed: Jun. 29, 2005

(65) Prior Publication Data

US 2006/0018890 A1 Jan. 26, 2006

Related U.S. Application Data

(60) Provisional application No. 60/584,830, filed on Jul. 1, 2004.

(51) Int. Cl.
*A01N 63/00* (2006.01)
*C12N 1/20* (2006.01)

(52) U.S. Cl. ................ 424/93.3; 435/252.4; 435/252.9; 426/61

(58) Field of Classification Search ........................ None
See application file for complete search history.

(56) References Cited

U.S. PATENT DOCUMENTS

| | | | |
|---|---|---|---|
| 4,873,229 A * | 10/1989 | Deya et al. ..................... 514/54 |
| 5,032,399 A | 7/1991 | Gorbach et al. | |
| 5,840,318 A | 11/1998 | Marshall et al. | |
| 6,203,797 B1 | 3/2001 | Perry | |
| 6,461,607 B1 | 10/2002 | Farmer | |
| 6,506,380 B1 | 1/2003 | Isolauri et al. ........... 424/93.45 |
| 6,613,549 B2 | 9/2003 | Reid et al. ................ 435/93.45 |
| 6,696,057 B1 | 2/2004 | Bojrab | |
| 2003/0031659 A1 | 2/2003 | Farmer | |
| 2003/0118571 A1 | 6/2003 | Reid et al. | |
| 2003/0180260 A1 | 9/2003 | Clancy et al. | |
| 2003/0180272 A1 | 9/2003 | Isolauri et al. | |
| 2003/0215467 A1 | 11/2003 | Collins et al. | |
| 2004/0057965 A1 | 3/2004 | Clancy et al. | |
| 2004/0115178 A1 | 6/2004 | Schiffrin et al. | |
| 2004/0147010 A1 | 7/2004 | Vidal et al. | |
| 2004/0197304 A1 | 10/2004 | Chen et al. | |
| 2004/0208863 A1 | 10/2004 | Versalovic et al. | |
| 2004/0219157 A1 | 11/2004 | Rochat et al. | |
| 2004/0265290 A1 | 12/2004 | Stadler et al. | |
| 2004/0265291 A1 | 12/2004 | Drake et al. | |
| 2005/0180961 A1 | 8/2005 | Pecquet et al. | |
| 2006/0018890 A1 | 1/2006 | Isolauri et al. | |
| 2008/0085267 A1 | 4/2008 | Herz et al. | |
| 2008/0118483 A1 | 5/2008 | Herz et al. | |
| 2008/0118484 A1 | 5/2008 | Herz et al. | |
| 2008/0118485 A1 | 5/2008 | Herz et al. | |
| 2008/0131413 A1 | 6/2008 | Herz et al. | |

FOREIGN PATENT DOCUMENTS

| | | |
|---|---|---|
| EP | 1364586 A1 | 5/2002 |
| JP | 09 002959 A | 1/1997 |
| JP | 2002 332242 A | 11/2002 |
| WO | WO 97/00078 | 1/1997 |
| WO | WO 98/36745 A2 | 8/1998 |
| WO | WO 00/35443 A1 | 6/2000 |
| WO | WO 01/32836 | 5/2001 |
| WO | WO 01/97822 A1 | 12/2001 |
| WO | WO 2004/069178 A2 | 8/2004 |
| WO | WO 2006/007526 A1 | 1/2006 |

OTHER PUBLICATIONS

Npochinda et al., J Med Assoc Thai. Nov. 2002;85 Suppl 4:S1225-31.*
Rulis: http://www.cfsan.fda.gov/~rdb/opa-g049.html, Mar. 19, 2002.*
Article by Journal of Nutritional Biochemistry, 2002, vol. 13, pp. 364-369 by P. Kankaanpää et al. entitled Influence of probiotic supplemented infant formula on composition of plasma lipids in atopic infants.
Article by BMJ, 2001, vol. 322, pp. 1-5 by K. Hatakka et al. entitled Effect of long term consumption of probiotic milk on infections in children attending day care centres: double blind, randomised trial. Online at bmj.com.
Article by American Journal of Clinical Nutrition, 2004, vol. 79 pp. 261-267, by J. Saavedra et al. entitl4ed Long-term consumption of infant formulas containing live probiotic bacteria: tolerance and safety[1-3].
Article by Journal of Dairy Science, 1999, vol. 82 pp. 649-660 by M.V. Tejada-Simon et al., entitled Ingestion of Yogurt Containing *Lactobacillus acidophilus* and *Bifidobacterium* to Potentiate Immunoglobulin A Responses to Cholera Toxin in Mice.

(Continued)

*Primary Examiner*—Irene Marx
(74) *Attorney, Agent, or Firm*—Waddey & Patterson, P.C.; James R. Cartiglia

(57) ABSTRACT

The present invention is directed to a novel method for preventing or treating respiratory infections and acute otitis media in infants. The method comprises the administration of a therapeutically effective amount of a *Bifidobacteria* strain and an adherence-promoting probiotic, such as LGG, to the infant.

11 Claims, 2 Drawing Sheets

OTHER PUBLICATIONS

Article by Pediatrics, 1997, vol. 100 No. 4, pp. 1-8 by L. Duffy et al. entitled Exclusive Breastfeeding Protects Against Bacterial Colonization and Day Care Exposure to Otitis Media. Online at http://www.pediatrics.org/cgi/content/full/100/4/e7.

Article from Clinical and Experimental Allergy, 2000, vol. 30, pp. 1604-1610 by E. Isolauri et al. entitled Probiotics in the management of atopic eczema.

Article from Monatsschr Kinderheilkd, 2003, vol. 151(Suppl. 1), pp. S27-S30 by E. Isolauri entitled Probiotics in the treatment and prevention of allergies.

Article by The Society for Applied Microbiology—Letters in Applied Microbiology, 2000, vol. 30, pp. 10-13 by A.C. Ouwehand et al. entitled The mucus binding of *Bifidobacterium lactis* Bb12 is enhanced in the presence of *Lactobacillus* GG and *Lact. delbrueckii* subsp. *bulgaricus*.

Editorials by BMJ, 2001, vol. 322, pp. 1318-1319 by C. A. Wanke entitled Do Probiotics prevent childhood illnesses.

Article by Clinical and Diagnostic Laboratory Immunology, 2001, vol. 8, No. 2, pp. 293-296 by M. Juntunen et al. entitled Adherence of Probiotic Bacteria to Human Intestinal Mucus in Healthy Infants and during Rotavirus Infection.

Article by American Journal of Clinical Nutrition, 2003, vol. 77, pp. 517-520 by U. Glück et al. entitled Ingested Probiotics reduce nasal colonization with pathogenic bacteria (*Staphylococcus aureus*, *Streptococcus pneumoniae*, and β-hemolytic streptococci)[1-3].

Article by American Journal of Clinical Nutrition, 2001, vol. 73(Suppl), pp. 1147-1151 by J. Saavedra entitled Clinical applications of probiotic agents[1-3].

Article by Applied and Environmental Microbiology, 1997, vol. 63, No. 9, pp. 3394-3398 by K. Kimura et al. entitled Analysis of Fecal Populations of *Bifidobacteria* and *Lactobacilli* and Investigation of the Immunological Responses of Their Human Hosts to the Predominant Strains.

Article by Pediatrics, 1999, vol. 104, No. 5, pp. 1-4 by T. Arvola et al. entitled Prophylactic *Lactobacillus GG* Reduces Antibiotic-Associated Diarrhea in Children with Respiratory Infections: A Randomized Study.

Article by Editorial Commentary—CID, 2001, vol. 32 pp. 1577-1578 by S. Salminen et al. entitled Probiotics-Demonstrating Efficacy in Clinical Settings.

Clinical Practice Guideline by American Academy of Pediatrics American of Family Physicians, entitled Diagnosis and Management of Acute Otitis Media.

Pamphlet organized by European Society for Paediatric Gastroenterology, Hepatology and Nutritioin (ESPGHAN), 2004 entitled 2nd World Congress of Pediatric Gastroenterology, Hepatology and Nutrition.

Pamphlet entitled LGG Summatim *Lactobacillus* GG and its health effects published by Valio Ltd, R&D, 2002, second edition.

Pamphlet entitled Health Benefits of *Lactobacillus* GG by Valio Ltd, 2003.

Article from Clinical and Diagnostic Laboratory Immunology, Mar. 1999; vol. 6, pp. 186-192 by H. Yasui et al., entitled Protection Against Influenza Virus Infection of Mice Fed.

Article by British Journal of Nutrition, 2002; vol. 88, Suppl. 1, pp. S59-S66 by M. de Vrese et al., entitled Probiotics and non-intestinal infectious conditions.

Article from Clinical and Diagnostic Laboratory Immunology, May 2001, pp. 593-597 by T. Hori et al., entitled Effect of Intranasal Administration of *Lactobacillus casei* Shirota on Influenza Virus Infection of Upper Respiratory Tract in Mice.

Article by Microbial Ecology in Health and Disease, 1992, vol. 5, pp. 155-162 by H. Yasui et al. entitled Detection of *Bifidobacterium* Strains that Induce Large Quantities of IgA.

Agostoni C et al., *Probiotic Bacteria in Dietetic Products for Infants: A Commentary by the ESPGHAN Committee on Nutrition*, Journal of Pediatric Gastroenterology and Nutrition, Apr. 2004, vol. 38, pp. 365-374.

Angelov, Alexander, *Eczema*, Natren The Probiotic Specialist Recognized Worldwide. [Online] http://www.natren.com/pages/eczema.asp.

Article entitled *Bacterial DNA Reduced Inflammation in Mice*, IBDanswers: Crohn's Disease, Colitis and Inflammatory Bowel Disease—Bacterial DNA, 2004. [Online] http://www.ibdanswers.com/Members/ScooterGirl/probiotics-2004.

Article entitled *Beneficial Bacteria (Probiotics) May Halt Allergies in Babies*, The Lancet, 2001, vol. 357, pp. 1076-1079. [Online] http:/www.mercola.com/2001/apr/14/probiotics.htm.

Article entitled *Beneficial Bacteria in Pregnancy May Reduce Infant Eczema*, 2002. [Online] http://www.numarkpharmacists.com/nw/page_nw_bacteria_reduce_infant_eczema.html.

Article entitled *Probiotics for mothers may boost infant immunity*, 2004. [Online] http://www.nutraingredients.com/news/news-NG.sasp?n_52616-probiotics-for-mothers.

Article entitled *Probiotics, Friendly Flora, Probiotic Bacteria*, 2003. [Online] http://www.1.stvitality.co.uk/az/probiotics/archive.htm.

Article entitled *Probiotic-Treated Mothers Confer Immunity on Infants*. [Online] http://www.vrp.com/art/743/asp, 2004.

Article entitled *Two Studies Support Probiotics*, 2002. [Online] http://us.pampers.com/en_US/content/type/105/contentId/13112.do.

Article entitled *What is an allergic reaction?*, [Online] http://www.air.linn.ia.us/pollen/reaction.htm.

Article published by the Art International Training Seminars Jun. 2003.

Auestad, N., et al., *Milk-substitutes comparable to rat's milk; their preparation, composition, and impact on development and metabolism in the artificially reared rat*, Br. J. Nutr., 1989, 61, pp. 495-518.

Baena-Cagnani, C., et al., *Role of food allergy in asthma in childhood*, Allergy and Clinical Immunology, 2001, vol. 1, pp. 145-149.

Bai, Al-Ping et al., *Probiotics inhibit TNF-a-induced interleukin-8 secretion of HT29 cells*, World Journal of Gastroenterology, 2004, vol. 10(3), pp. 455-457.

Blaser, K., et al., *Interleukin-10, T regulatory cells and specific allergy treatment*, Clinical and Experimental Allergy, 2004, vol. 34, pp. 328-331.

Boyle, RJ, et al., *Can allergic diseases be prevented prenatally?*, Allergy, 2006, pp. 1-9. [Online] Retrieved from internet: URL: doi: 10.1111/j. 1398-9995.2006.01113.x on Aug. 2, 2006.

Breese, E., et al., *TNFa Secreating Cells in Normal and Diseased Human Intestine*, Adv Exp Med Biol, 1995; 37aB: pp. 821-824.

Carlson, SE, et al., *Lower Incidence of Necrotizing Enterocolitis in Infants Fed a Preterm Formula with Egg Phospholipids*, Pediatric Research, Williams and Wilkins, vol. 44, No. 4, Oct. 1998, pp. 491-498.

Castagliuolo, I., et al., *Clostrigium difficile Toxin A Stimulates Macrophage-Inflammatory Protein-2 Production in Rat Intestinal Epithelial Cells*[1], J Immunol, 1998; 160(12), pp. 6039-6045.

Cerra, FB, et al., *Septic Autocannibalism—A Failure of Exogenous Nutritional Support*, Ann Surg, 1980, 192:pp. 570-580.

Claud, EC., et al., *Hypothesis: inappropriate colonization of the premature intestine can cause neonatal necrotizing enterocolitis*, The FASEB Journal, 2001; vol. 15, pp. 1398-1403. [Online] http://www.fasebj.org/cgi/content/full/15/8/1398.

Claud, Erika C., et al., *Developmentally regulated IkB expression in intestinal epithelium and susceptibility to flagellin-induced inflammation*, PNAS, May 11, 2004; vol. 101, No. 19, pp. 7404-7408. [Online] http://www.pnas.oro/cgi/content/full/101/19/7404.

Colavita, AM, et al., *Kinetics of IL-10 production after segmental antigen challenge of atopic asthamatic subjects*, The Journal of Allergy and Clinical Immunology, 2000, vol. 106, No. 5, pp. 880-886.

Collins, M David, et al., *Probiotics, prebiotics, and synbiotics: approaches for modulating the microbial ecology of the gut*[1,2], The American Journal of Clinical Nutrition, May 1999, vol. 69, No. 5, 1052S-1057S. [Online] http://www.ajcn.org/cgi/content/full/69/5/1052S.

Daig, RT, et al., *Increased interleukin 8 expression in the colon mucosa of patients with inflammatory bowel disease*, Gut, 1996; 38: pp. 216-222.

Dani, C., et al., *Probiotics Feeding in Prevention of Urinary Tract Infection, Bacterial Sepsis and Necrotizing Enterocolitis in Preterm Infants*, Biol Neonate, 2002; 82: 103-108.

Das, Undurtin N., *A Perinatal Strategy to Prevent Coronary Heart Disease*, Nutrition (Burbank, Los Angeles County, CA), Nov.-Dec. 2003, vol. 19, No. 11-12, Nov. 2003, pp. 1022-1027.

De Bont, ES, et al., *Diagnostic value of plasma levels of tumor necrosis factor a (TNFa) and interleukin 6 (IL-6) in newborns with sepsis*, Acta Paediatr Jpn, 1994, 83: 696-699.

Deitch, EA, et al., *Evidence Favoring the Role of the Gut as a Cytokine-Generating Organ in Rats Subjected to Hemorrhagic Shock*, Shock, 1994, vol. 1, No. 2, pp. 141-145.

Deplancke, B, et al., *Microbial modulation of innate defense: goblet cells and the intestinal mucus layer* [1-3], Am J Clin Nutr 2001; 73 (suppl): 1131-1141.

Dudley, DJ, *Pre-term labor: an intra-uterine inflammatory response syndrome?* [1], J Reproductive Immunology, 1997; 36: pp. 93-109.

Duffy, LC, *Interactions Mediating Bacterial Translocation in the Immature Intestine* [1,2], J Nutr, 2000; 130: pp. 432-436.

ESPCHAN Committee on Nutrition, *Probiotic Bacteria in Dietetic Products for Infants: A Commentary by the ESPGHAN Committee on Nutrition*, Journal of Pediatric Gastroenterology and Nutrition, 2004, vol. 38, No. 4, pp. 365-374.

Mattsson, Eva, et al., *Highly Purified Lipoteichoic Acid from Staphylococcus Aureus Induces Procoagulant Activity and Tissue Factor Expression in Human Monocytes but Is a Weak Inducer in Whole Blood: Comparison with Peptidoglycan*, Infection and immunity, Jul. 2004, vol. 72, No. 7, pp. 4322-4326 [Online] http://iai.asm.org/cgi/content/full/72/7/4322.

Fischer, CP, et al., *Hepatic Uptake of Glutamine and Other Amino Acides During Infection and Inflammation*, Shock, 1995; 3(5): pp. 315-322.

Fong, YM, et al., *The Acute Splanchnic and Peripheral Tissue Metabolic Response to Endotoxin in Humans*, J Clin Invest, 1990; 85: pp. 1896-1904.

Ghisolfi, J., et al., *Infant Formula Supplement With Probiotics or Prebiotics: Never, Now, or Someday?*, Journal of pediatric Gastroenterology and Nutrition, 2002; 35(4): pp. 467-468.

Gorbach, SL, *Probiotics and Gastrointestinal Health*, American Journal of Gastroenterology, vol. 95, No. 1 suppl., Jan. 2001, pp. S2-S4.

Reid, Gregor, et al., *Potential Uses of Probiotics in Clinical Practice*, Clinical Microbiology Reviews, Oct. 2003, vol. 16(4), pp. 658-672. [Online] http://www.pubmedcentral.nih.gov/articlerender.fcgi?artid=207122.

Hall, WG, *Weaning and Growth of Artificilly-Reared Rats*, Science, 1975; 190(4221): pp. 1313-1315.

Haller, D, et al., *Non-pathogenic bacteria elicit a differential cytokine response by intestinal epithelial cell/leucocyte co-cultures*, Gut, 2000; 47(1): pp. 79-87.

Harmsen, HJ, et al., *Analysis of Intestinal Flora Development in Breast-fed and Formula-fed Infants by Using Molecular Identification and Detection Methods*, J Pediatr Gastroenterol Nutr 2000; 30(1), pp. 61-67.

Harris, Ed, *Differential PCR and DNA Microarrays: The Modern Era of Nutritional Investigations*, Nutrition, 2000; 16(7-8): pp. 714-715.

Heaton, T, et al., *An immunoepiemiological approach to asthma: identification of in-vitro T-cell response patterns associated with different wheezing phenotypes in children*, The Lancet, 2005, vol. 365, pp. 142-149. [Online] www.thelancet.com.

Herz, U, et al., *Prenatal Sensitization in a Mouse Model*, American Journal of Respiratory and Critical Care Medicine, 2000, vol. 162, pp. S62-S65.

Hooper, LV, et al., *How Host-Microbial Interactions Shape the Nutrient Environment of the Mammalian Intestine*, Annu Rev Nutr, 2002; 22: pp. 283-307.

Hoyos, AB, *Reduced Incidence of necrotizing Enterocolitis Associated with Enteral Administration of Lactobacillus Acidophilus and Bifidobacterium Infantis to Neonates in an Intensive Care Unit*, Int J Infect Dis, 1999; 3(4): pp. 197-202.

Illi, S, et al., *The natural course of atopic dermatitis from birth to age 7 years and the association with asthma*, Journal of Allergy and Clinical Immunology, 2004, vol. 113, No. 5, pp. 925-931.

International Search Report of the International Searching Authority for application No. PCT/US2006/010321, International filing date Mar. 22, 2006. Date of mailing Aug. 14, 2006.

International Search Report of the International Searching Authority for application No. PCT/US2006/010415, International filing date Mar. 22, 2006. Date of mailing Aug. 14, 2006.

International Search Report of the International searching Authority for application No. PCT/US2006/010418, International filing date Mar. 22, 2006. Date of mailing Aug. 17, 2006.

Isolauri, E, et al., *Probiotics: effects on immunity* [1-3], American Journal Clinical Nutrition, 2001; vol. 73(suppl), pp. 444S-50S.

Isolauri, E, *Probiotics in human disease* [1,2,3], American Journal of clinical Nutrition, Jun. 2001, vol. 73, No. 6, pp. 1142S-1146S. [Online] http://www.ajcn.org/cgi/content/full/73/6/11428S.

Jiang, J, et al., *Kinetics of Endotoxin and Tumor Necrosis Factor Appearance in Portal and Systemic Circulation After Hemorrhagic Shock in Rats*, Ann Surg 1995; 221(1): p. 100-106.

Kaila, M, et al., *Fatty acids in substitute formulas for cow's milk allergy*, Allergy, Munskgaard, vol. 54, No. 1, 1999, pp. 74-77.

Kalliomaki, M, et al., *Probiotics in primary prevention of atopic disease: A randomized placebo-controlled trial*, The Lancet, 2001, vol. 357, pp. 1076-1079. [Online] http://www.health-report.co.uk/probioticsatopicdisease.htm.

Vidal, Karine, et al., *Lipoteichoic Acids from Lactobacillus Johnsonii Strain La1 and Lactobacillus Acidophilus Strain LA10 Antagonize the Responsiveness of Human intestinal Epithelial HT29 Cells to Lipopolysaccharide and Gram-negative Bacteria*, Infection and Immunity, Apr. 2002, vol. 70, No. 4, pp. 2057-2064. [Online] http://isi.asm.org/cgi/content/full/70/4/2057.

Kirjavainen, PV, et al., *Aberrant composition of gut microbiota of allergic infants: a target of bifidobacterial therapy at weaning?*, Gut Journal, 2002, vol. 51, pp. 51-55. [Online] http://www.gurjnl.com.

Lu, L, et al., *Pathologic and physiologic interactions of bacteria with the gastrointestinal epithelium* [1-3], Am J Clin Nutr, 2001; 73(suppl); pp. 1124-1130.

Mainous, MR, et al., *The Gut: A Cytokine-Generating Organ in Systemic Inflammation?*, Shock, 1995; vol. 4, No. 3, pp. 193-199.

Mainous, MR, et al., *Nutritional Support of the Gut: How and Why*, New Horiz, 1994, vol. 2, No. 2, pp. 193-201.

Majamaa, H, et al., *Lactic Acid Bacteria in the Treatment of Acute Rotavirus Gastroenteritis*, Journal of Pediatric Gastroenterology and Nutrition, vol. 20, No. 3, Apr. 1995, pp. 333-338.

Majamaa, H, et al., *Probiotics: A novel approach in the management of food allergy*, Journal of Allergy and Clinical Immunology, Mosby-Yearly Book, Inc., US, vol. 99, No. 2, 1997, pp. 179-185.

Marteau, Philippe R, et al., *Protection from gastrointestinal diseases with the use of probiotics* [1,2,3], American Journal of Clinical Nutrition, Feb. 2001, vol. 73, No. 2, pp. 430S-436S. [Online] http://www.ajcn.org/cgi/content/full/73/2/430S.

Martinez, FD, *Development of Wheezing Disorders and Asthma in Preschool Children*, Pediatrics, 2002, vol. 109, No. 2, pp. 362-367.

Martinez, FD, *Viruses and Atopic Sensitization in the First Years of Life*, American Journal of Respiratory and Critical Care Medicine, 2000, vol. 162, pp. S95-S99.

Matsuguchi, Tetsuya, et al., *Lipoteichoic Acids from Lactobacillus Strains Elicit Strong Tumor Necrosis Factor Alpha-Inducing Activities in Macrophages Through Toll-like Receptor 2*, Clinical and Dianostic Laboratory Immunology, Mar. 2003, vol. 10, No. 2, pp. 259-266. [Online] http://cdli.asm.org/cgi/content/full/10/2/259.

Mihrshahi, Seema, et al., *Eighteen-month outcomes of house dust mite avoidance and dietary fatty acid modification in the Childhood Asthma Prevention Study (CAPS)*, Journal of Allergy and Clinical Immunology, vol. 11, No. 1, Jan. 2003, pp. 162-168.

Millar, M, et al., *Probiotics for preterm infants?*, Arch Dis Child Fetal Neonatal Education, 2003, vol. 88, pp. F354-F358. [Online] http://archdischild.com.

Morecroft, JA, et al., *Necrotizing enterocolitis—multisystem organ failure of the newborn?*, Acta Paedr, 1994, suppl 396, pp. 21-23.

Murch, SH, *Toll of allergy reduced by probiotics*, Lancet, 2001; 357: 1057-1059.

Nagakura, T, et al., *Dietary supplementation with fish oil rich in omega-3 polyunsaturated fatty acids in children with bronchial asthma*, European Respiratory Journal, vol. 16, No. 5, Nov. 2000, pp. 861-865.

Nelson, KB, et al., *Neonatal Cytokines and Coagulation Factors in Children with Cerebral Palsy*, Ann Neurol, 1998; 44(4): pp. 665-675.

Pena, Jeremy Andrew, et al., *Lactobacillus rhamnosus GG decreases TNF-alpha production in lipopolysaccharide-activated murine macrophages by a contact-independent mechanism*, Cellular Microbiology, Blackwell Science, vol. 5, No. 4, Apr. 2003 pp. 277-285.

Bourlioux, Pierre, et al., *The intestine and its microflora are partners for the protection of the host: report on Danone Symposium "The Intelligent Intestine,"* held in Paris, Jun. 14, 2002[1,2], American Journal of Clinical Nutrition, Oct. 2003, vol. 78, No. 4, pp. 675-783. [Online] http://www.ajcn.org/cgi/content/full/78/4/675.

Rautava, S, et al., *Probiotics during pregnancy and breast-feeding might confer immunomodulatory protection against atopic disease in the infant*, The Journal of Allergy and Clinical Immunology, 2002, vol. 109, No. 1, pp. 119-121. [Online} http://www2.us.elsevierhealth.com/scripts/om.dl1/serve.

Remick, D, *Lung and gut injury induced by tumor necrosis factor*, Res Immunol, 1993; 144, pp. 326-331.

Stuyt, Rogier JL, et al., *Differential Roles of Interleukin-18 (IL-18) and IL-12 for Induction of Gamma Interferon by Staphylococcal Cell Wall Components and Superantigens*, Infection and Immunity, Aug. 2001, vol. 69, No. 8, pp. 5025-5030.

Rubaltelli, Firmino F, et al., *Probiotics Feeding Prevents Necrotizing Enterocolitis in Preterm Infants: A Prospective Double-Blind Study*, Pediatric Research, vol. 47, No. 4, part 2, Apr. 2000, p. 346A.

Sansonetti, PJ, et al., *Interleukin-8 Controls Bacterial Transepithelial Translocation at the Cost of Epithelial Destruction in Experimental Shigellosis*, Infect Immun, 1999; 67(3): p. 1471-1480.

Schrezenmeir, Jurgen, et al., *Probiotics, prebiotics, and synbiotics—approaching a definition*[1,2,3], American Journal ofClinical Nutrition, Feb. 2001, vol. 73, No. 2, pp. 361S-364S. [Online] http://www.ajcn.org/cgi/content/full/73/2/361S.

Sherman, Michael P, et al., *Neonatal small bowel epithelia: enhancing anti-bacterial defense with lactoferrin and Lactobacillus GG*, Biometals, vol. 17, No. 3, Jun. 2004, pp. 285-289.

Sugawara, Shunji, et al., *Lipoteichoic Acid Acts as an Antagonist and an Agonist of Lipopolysaccharide on Human Gingival Fibrobasts and Monocytes in a CD14-dependent Manner*, Infection and Immunity, Apr. 1999, vol. 67, No. 4, pp. 1623-1632. [Online] http://iai.asm.org/cgi/content/full/67/4/1623.

Silen, ML, et al., *Cachectin / Tumor Necrosis Factor Production by Fetal and Newborn Rat Hepatic Macrophages*, J Pediatr Surg, 1989; 24(1), pp. 34-38.

Stratakis, CA, et al., *Interleukin-6 elevation in critically ill infants with sepsis and necrotizing enterocolitis*, Journal of Pediatrics, 1994: 125(3), p. 504. [Online] http://www2.us.elsevierhealth.com.

Umetsu, DT, et al., *Interleukin-10, The Missing Link in Asthma Regulation?*, American Journal of Respiratory Cell and Molecular Biology, 1999, vol. 21, p. 562-563.

Van Der Poll, T, et al., *Release of Soluble Receptors for Tumor necrosis Factor in Clinical Sepsis and Experimental Endotoxemia*, J Infect Dis, 1993; 168, p. 955-960.

Vidal, Karine, et al., *Lipoteichoic Acids from Lactobacillus Johnsonii Strain La1 and Lactobacillus Acidophilus Strain La10 Antagonize the Responsiveness of Hman Intestinal Epithelial HT29 Cells to Lipopolysaccharide and Gram-negative Bacteria*, Infection and Immunity, Apr. 2002, vol. 70, No. 4, pp. 2057-2064. [Online] http://iai.asm.org/cgi/content/full/70/4/2057.

Viljanen, M, et al., *Induction of inflammation as a possible mechanism of probiotic effect in atopic eczema-dermatitis syndrome*, Journal of Allergy and Clinical Immunology, Mosby-Yearly Book, Inc, US, vol. 115, No. 6, Jun. 2005, pp. 1254-1259.

Vince, G, *Probiotic bacteria "treat eczema in babies"*, [Online] http://www.newscientist.com/article.ns?id_dn2446, 2002.

Walker, WA, *Development of the Intestinal Mucosal Barrier*, J Pediatr Gastroenterol Nutr, 2002; 34(suppl 1), pp. 33-39.

Wang, JE, et al., *Peptidoglycan and Lipoteichoic Acid from Staphylococcus aureus Induce Tumor Necrosis Factor Alpha, Interleukin 6 (IL-6), and IL-10 Production in Both T-Cells and Monocytes in a Human Whole Blood Model*, Infection and Immunity, Jul. 2000, vol. 68, No. 7, pp. 3965-3970. [Online] http://iai.asm.org/cgi/content/full/68/7/3965.

Warner, JO, *The early life origins of asthma and related allergic disorders*, Archives of Diseases in Childhood, 2004, vol. 89, pp. 97-102.

Weil, GJ, et al., *Prenatal Allergic Sensitization to Helminth Antigens in Offspring of Parasite-infected Mothers*, Journal of Clinical Investigation, 1983, vol. 71, p. 1124-1129.

Written Opinion of the International Searching Authority for application No. PCT/US2006/010415, International filing date Mar. 22, 2006. Date of mailing Aug. 14, 2006.

Written Opinion of the International Searching Authority for application No. PCT/US2006/010418, International filing date Mar. 22, 2006. Date of mailing Aug. 17, 2006.

Written Opinion of the International Searching Authority for application No. PCT/US2006/010321, International filing date Mar. 22, 2006. Date of mailing Aug. 14, 2006.

Xu, Jian, et al., *Honor thy symbionts*, PNAS, Sep. 2, 2003, vol. 100, No. 18, pp. 10452-10459. [Online] http://www.pnas.org/cgi/content/full/100/18/10452.

Yamasaki, Y, et al., *Involvement of Cytokine Production in Pathogenesis of Transient Cerebral Ischemic Damage*, Keio J Med, 1996; 45(3): p. 225-9.

Isolauri, E, et al., *Lactobacillus casei Strain GG Reverses Increased Intestinal Permeability Induced by Cow Milk in Suckling Rats*, Gastroenterology 1993; 105:1643-1650.

* cited by examiner

METHOD FOR PREVENTING OR TREATING RESPIRATORY INFECTIONS AND ACUTE OTITIS MEDIA IN INFANTS USING *LACTOBACILLUS RHAMNOSUS* LGG AND *BIFIDOBACTERIUM LACTIS* BB-12

This application claims priority to U.S. Provisional Application 60/584,830 filed Jul. 1, 2004, which is incorporated by reference herein in its entirety.

BACKGROUND OF THE INVENTION (1) Field of the Invention

The present invention relates generally to a method for preventing or treating respiratory infections and acute otitis media in infants.

(2) Description of the Related Art

Respiratory tract infections are extremely common, especially among infants. In the first year of life, infants are prone to recurrent respiratory tract infections, often experiencing between three and six infections during that year alone. About 6% of infants less than one year of age are hospitalized for lower respiratory tract infections each year in the United States alone.

Respiratory infections and their symptoms can range from mild to severe, depending on the type of virus and the location of the infection. Upper respiratory infections often manifest themselves as common colds, causing inflammation and swelling of the lining of the nose, throat and sinuses. Influenza, commonly known as the flu, is a highly contagious viral infection of the upper respiratory tract. Symptoms of the flu include fever, chills, headache, muscle aches, dizziness, cough, sore throat, runny nose, nausea and diarrhea. Another upper respiratory infection, croup, causes a very deep cough and varying degrees of breathing difficulty, primarily when inhaling.

Lower respiratory infections are generally considered more serious than upper respiratory infections. Respiratory syncytial virus (RSV) is the most frequent cause of lower respiratory tract infections in infants and children younger than four years of age. Van Woensel, J., et al., *Viral Lower Respiratory Tract Infection in Infants and Young Children*, BMJ 327:36-40 (2003). This is such a common virus that virtually all children have been infected with RSV by the age of three. In most infants and children, RSV is a mild respiratory infection that is indistinguishable from a common cold. It usually causes nasal stuffiness, nasal discharge and cough.

Protection against RSV involves both T- and B-cell responses, antibody responses (IgM, IgG, and IgA), as well as other immune system responses that are activated by bacterial and viral infections. A link between RSV infection in infancy and the development of recurrent wheezing, asthma and atopy later in childhood has been suggested. Thus, limiting RSV infections could prevent serious respiratory complications which extend well into childhood.

Bronchitis is a lower respiratory infection that affects the bronchial tubes, causing narrowing and swelling due to viral inflammation. Bronchiolitis is similar to bronchitis, but occurs primarily in infants. It is an inflammation of the smaller caliber tubes of the branching network of brochi. The infection causes labored breathing, frequent and dramatic coughing and wheezing and may require hospitalization.

The lower respiratory infection that is probably the most serious for infants is pneumonia. Pneumonia is caused by an infection in the alveoli, causing them to become filled with fluid, often of a thick purulent nature, that interferes with proper exchange of carbon dioxide. The severity of the pneumonia will depend on the amount of lung tissue involved.

Most upper and lower respiratory infections are caused by viruses for which no specific prevention or treatment is currently available. Some respiratory infections, including influenza, may be prevented with a vaccination. However, even when vaccinations are developed for specific respiratory infections, they are expensive and not universally available. Similarly, drugs to treat these infections have limited availability and are expensive. Thus, it would be useful to provide a non-medicinal method for the treatment or prevention of respiratory infections in infants.

Frequent respiratory tract infections are often associated with acute otitis media (AOM), also known as middle ear infection. AOM is characterized by an acute, short course of inflammation and fluid in the middle ear. AOM can be accompanied by rhinitis, cough, fever, sore throat, ear ache, hypacusis, restlessness, irritability, loss of appetite, vomiting or diarrhea. Purulent otorrhea through a perforated tympanic membrane is also considered to constitute AOM.

Fifty percent of children have had at least one episode of AOM by one year of age. Eighty percent of children have had at least one episode by their third birthday. Between one and three years, 35% of children will have had recurrent episodes of AOM.

AOM can be caused by viruses or bacteria. The most common bacterial strains that cause AOM are *Streptococcus pneumoniae* (35% of cases), *Haemophilus influenzae* (30% of cases) and *Moraxella catarrhalis* (10% of cases). Because bacterial strains frequently cause the infection, AOM is commonly treated through the administration of antibiotics. In fact, more antibiotic prescriptions are written for AOM than for any other disease in infancy. The disadvantage to this widespread antibiotic treatment is the development of antibiotic resistance. For example, between 20% and 40% of *S. pneumoniae* strains are resistant to penicillins and cephalosporins. Similarly, between 30% and 40% of *H. influenzae* and about 90% of *M. catarrhalis* strains have developed antibiotic resistance.

Due to the prevalence of antibiotic resistance among pathogenic bacteria, the American Academy of Pediatrics and the American Academy of Family Physicians have developed guidelines suggesting a limited prescription of antibiotics for AOM. *American Academy of Pediatrics and the American Academy of Family Physicians, Subcommittee on the Management of Acute Otitis Media, Clinical Practice Guideline* (March 2004), available at http://www.aafp.org/PreBuilt/final_aom.pdf. Therefore, as antibiotic therapies become more limited, it is important to provide alternative therapies to decrease the incidence of this painful and serious condition in infants and young children.

In a meta-analysis of data from multiple studies, results indicate that breastfeeding may have a positive effect on the frequency of both infant respiratory infection and AOM. Specifically, one study indicated that the feeding of many currently available infant formulas may be associated with a 3.6-fold increase in risk of infant hospitalization for respiratory infection when compared to at least four months of exclusive breastfeeding. Bachrach, V., et al., Arch. Pediatr. Adolesc. Med. 57:237-43 (2003). Additionally, infants who are breastfed have been shown to have significantly fewer (about 50%) episodes of AOM than do infants who are exclusively formula-fed. Duffy, et al., Pediatr. 100(4):E7 (1997). These differences may be attributed to the fact that human milk promotes the growth of beneficial bacteria such as *Lactobacilli* and *Bifidobacteria*. Duffy, et al., Dig. Dis. Sci. 44(8): 1499-1505 (1999).

It has been shown that the microflora of breast-fed infants contains predominantly *Bifidobacteria*. In contrast, the microflora of formula-fed infants is more diverse, containing *Bifidobacteria* and *Bacteroides* as well as the more pathogenic species, *Staphylococcus, Escherichia coli*, and *Clostridia*. The varied species of *Bifidobacteria* in the stools of breast-fed and formula-fed infants differ as well. A variety of factors have been proposed as the cause for the different fecal flora of breast-fed and formula-fed infants, including the lower content and different composition of proteins in human milk, a lower phosphorus content in human milk, the large variety of oligosaccharides in human milk, and numerous humoral and cellular mediators of immunologic function in breast milk. Agostoni, et al., *Probiotic Bacteria in Dietetic Products for Infants: A Commentary by the ESPGHAN Committee on Nutrition*, J. Pediatr. Gastro. Nutr. 38:365-374 (April 2004). Regardless of the cause for the differing bacterial populations, it is clear that breast milk has a measurable benefit in the treatment or prevention of respiratory infections and AOM.

Both the American Academy of Pediatrics and World Health Organization advise mothers to breastfeed for between one and two years. In developed countries, however, these recommendations are sometimes difficult for working mothers to follow. In the United States, for example, 53% of lactating mothers introduce formula before their babies are a week old. By four months of age, 81% of infants receive formula on a regular basis. Fewer than 5% of American infants are being breastfed at twelve months of age. Wolf, J., Am. J. Pub. Health 93:2000-2010 (2003).

One way to encourage gut colonization with beneficial microorganisms in infants that are formula-fed is through the administration of probiotic bacteria. Probiotic bacteria are living microorganisms that exert beneficial effects on the health of the host. *Lactobacillus* spp. and *Bifidobacterium* spp. are among the common species of probiotics. Probiotics such as these have been shown effective in treating various gastrointestinal disorders.

For example, U.S. Pat. No. 6,613,549 to Reid relates to the use of probiotic microorganisms such as *Lactobacillus* and *Bifidobacterium* in treating intestinal infection in infants. The patent does not, however, teach any treatment of infections outside the intestinal tract. While probiotics have been effective in decreasing the incidence of diarrheal disease and rotaviral shedding in hospitalized infants, a probiotic combination of *B. lactis* and *S. thermophilus* did not show a significant effect in terms of decreasing the frequency of overall incidents for which healthcare attention was sought. Saavedra, et al., Am. J. Clin. Nutr. 79:261-67 (2004).

U.S. patent application Ser. Nos. 20040057965 and 20030180260 to Clancy, et al. describe the administration of an antigen and a probiotic to treat mucosal infections such as respiratory tract infections. Similarly, U.S. patent application Ser. No. 20040265291 to Drake, et al. relates to a method of inhibiting or reducing chronic or upper respiratory infection and ear infection through the administration of a bacteria, a bacteria nutrient, and an antimicrobial agent. These references, however, relate solely to adult administration and do not disclose the administration of probiotics to infants to treat respiratory tract infections or AOM.

The gut microflora in infants is known to be far less developed than that of an adult. While the microflora of an adult human consists of more than $10^{13}$ microorganisms and nearly 500 species, some being harmful and some being beneficial, the microflora of an infant contains only a fraction of those microorganisms, both in absolute number but also in species diversity. Because the bacterial populations and species vary so immensely between the gut of an infant and the gut of an adult, it cannot be assumed that a probiotic administration designed for an adult would necessarily be beneficial for an infant.

It would be beneficial, therefore, to provide a probiotic remedy for the treatment and or prevention of respiratory infections and AOM in infants.

SUMMARY OF THE INVENTION

Briefly, the present invention is directed to a novel method for preventing or treating respiratory infections in infants, comprising administering to the infant a therapeutically effective amount of at least one *Bifidobacterium* species in conjunction with at least one probiotic bacterial species that promotes the growth and adherence of the selected strain of *Bifidobacteria* in the intestine. In one embodiment, the *Bifidobacterium* species can be chosen from among the *Bifidobacteria* that demonstrate immunomodulatory properties. These species may include, for example, *B. bifidum, B. adolescentis, B. animalis, B. lactis, B. infantis, B. longum*, and *B. thermophilum*. A particular species useful in the present invention is *B. lactis* Bb-12.

In one embodiment, the probiotic that promotes *Bifidobacteria* adherence is a member of the *Lactobacillus* species, such as, for example, *L. rhamnosus* GG (LGG), *L. delbrueckii* subsp. *bulgaricus*, or a combination of both.

The present invention is also directed to a novel method for preventing or treating acute otitis media in infants, comprising administering to the infant a therapeutically effective amount of at least one *Bifidobacterium* species and at least one probiotic that promotes the growth and adherence of the selected species of *Bifidobacteria* to intestinal mucosa.

The invention is also directed to a novel method for preventing or treating recurrent respiratory infections and recurrent AOM infections in infants. The method comprises administering to the infant a therapeutically effective amount of at least one *Bifidobacterium* species and at least one probiotic that promotes the growth and adherence of the selected species of *Bifidobacteria* to intestinal mucosa.

Among the several advantages found to be achieved by the present invention is that it provides a method for preventing or treating respiratory infections in infants without the necessity of administering unavailable or costly medications or vaccinations. The invention also provides a method for preventing or treating AOM without the necessity of administering antibiotics that may cause resistance among pathogenic bacterial species.

DETAILED DESCRIPTION OF THE PREFERRED EMBODIMENTS

Figure 1:
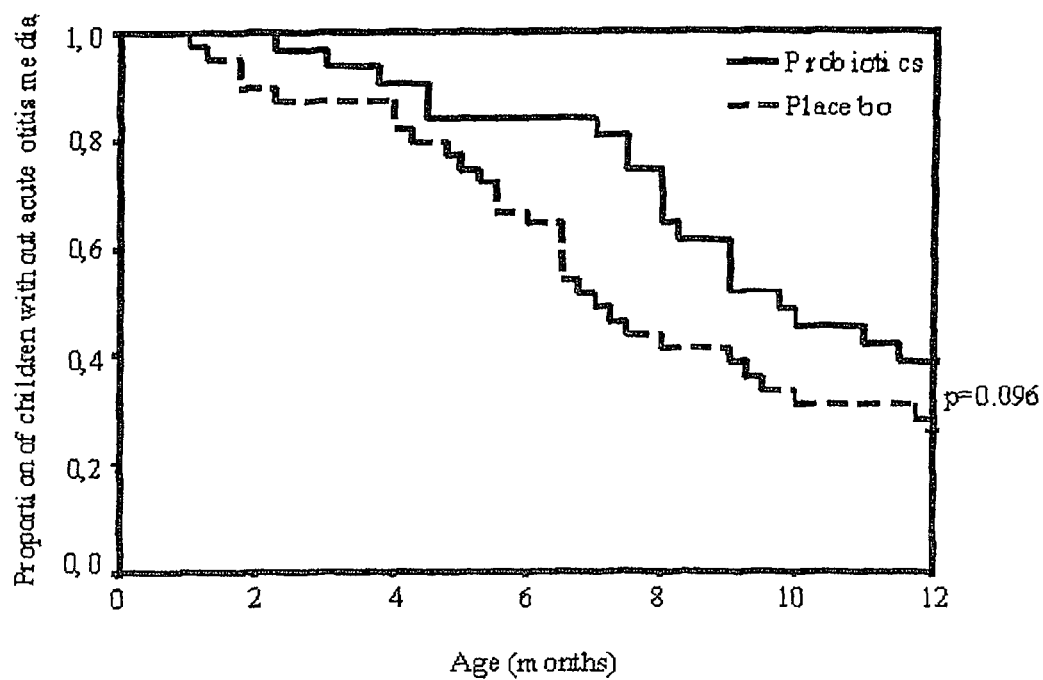
FIG. 1 is a graph indicating the effect of probiotic supplementation on the development of an AOM episode during the first year of life.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

DEFINITIONS

As used herein, the term "treating" means ameliorating, improving or remedying a disease, disorder, or symptom of a disease or condition.

The term "preventing" means stopping or hindering a disease, disorder, or symptom of a disease or condition through some action.

The terms "therapeutically effective amount" refer to an amount that results in an improvement or remediation of the disease, disorder, or symptoms of the disease or condition.

The term "infant" means a human that is less than about 2 years old.

The terms "respiratory infection" or "respiratory illness" mean a disease or infection affecting the group of organs responsible for carrying oxygen from the air to the bloodstream and for expelling carbon dioxide.

The term "probiotic" means a microorganism that exerts beneficial effects on the health of the host. It can be a live microbial fed supplement that beneficially affects the host by improving its intestinal microbial balance, a microbial preparation that contains live or dead bacteria, or a combination of both. Live organisms are often preferred, as they produce a complete array of antigens, reproduce to increase the number of such organisms in the intestinal environment to promote mucosal interaction, and may adhere to the intestinal tissues to better stimulate a mucosal immune response.

The term "prebiotic" means a non-digestible food ingredient that stimulates the growth and/or activity of probiotics.

The term "recurrent" means 3 or more occurrences of infection during one year.

As used herein, the term "infant formula" means a composition that satisfies the nutrient requirements of an infant by being a substitute for human milk. In the United States, the contents of an infant formula are dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

INVENTION

In accordance with the present invention, a novel method for preventing or treating respiratory infections in infants has been developed. The method comprises administering to the infant a therapeutically effective amount of at least one species of *Bifidobacteria*, such as Bb-12, and at least one probiotic, such as LGG, that promotes the adherence of the selected *Bifidobacterium* strain to the intestinal mucosa.

*Bifidobacteria* are gram-positive anaerobes that operate in the lower part of the digestive system. They are non-motile, non-spore forming and catalase-negative. They have various shapes, including short, curved rods, club-shaped rods and bifurcated Y-shaped rods. They are classified as lactic acid bacteria due to their production of lactic acid during carbohydrate fermentation.

In one embodiment of the present invention, the *Bifidobacterium* species can be chosen from among the *Bifidobacteria* that demonstrate immunomodulatory properties. These species may include, for example, *B. bifidum*, *B. adolescentis*, *B. animalis*, *B. lactis*, *B. infantis*, *B. longum*, and *B. thermophilum*. A particular strain of *Bifidobacteria* that is useful in the present invention is *B. lactis* Bb-12, available from Chr. Hansen Biosystems, located in Milwaukee, Wis.

In one embodiment of the invention, the probiotic that promotes the adherence of *Bifidobacteria* to the intestinal musoca can be a member of the genus *Lactobacillus*. *Lactobacilli* are gram-positive facultative anaerobes. They are non-spore forming and non-flagellated rod or coccobacilli. Any species of *Lactobacilli* known in the art can be used in this embodiment. For example, the adherence-promoting probiotic can be LGG, *L. delbrueckii* subsp. *bulgaricus*, or a combination of both.

LGG is a *Lactobacillus* strain isolated from healthy human intestinal flora. It was disclosed in U.S. Pat. No. 5,032,399 to Gorbach, et al., which is incorporated herein in its entirety, by reference thereto. LGG is resistant to most antibiotics, stable in the presence of acid and bile, and attaches avidly to mucosal cells of the human intestinal tract. It survives for 1 to 3 days in most individuals and up to 7 days in 30% of subjects. In addition to its colonization ability, LGG also beneficially affects mucosal immune responses. LGG is deposited with the depository authority American Type Culture Collection under accession number ATCC 53103.

*L. delbrueckii* are Gram-positive, facultatively anaerobic, non-motile and non-spore-forming, rod-shaped microorganisms. Like other lactic acid bacteria, *L. delbrueckii* are acid tolerant, cannot synthesize porphyrins, and possess a strictly fermentative metabolism with lactic acid as the major metabolic end product. *L. delbrueckii* species contain three subspecies, *L. delbrueckii* subsp. *delbrueckii*, *L. delbrueckii* subsp. *lactis*, and *L. delbrueckii* subsp. *bulgaricus*.

Generally, the adherence rate of selected *Bifidobacteria* to intestinal mucosa is around 18%. Previous studies have indicated that certain bacterial species can promote the adherence of *Bifidobacteria* to the intestinal mucosa. Juntunen, M. et al. Clin. Diag. Lab. Immunol. 8:293-96 (2001). In the presence of two *Lactobacillus* species in particular, LGG (ATCC No. 53103) and *L. delbrueckii* subsp. *bulgaricus* (available from Valio Ltd., Finland), the adherence of *Bifidobacteria* increased from 18% to 44% and 45%, respectively. Id. Though not wishing to be bound by this or any other theory, it is believed that these *Lactobacillus* strains coaggregate and thereby increase the adherence of *Bifidobacteria* to the intestinal mucosa and their residence time within the intestine.

According to the method of the present invention, when a strain of *Bifidobacteria* is provided in combination with at least one adherence-promoting probiotic, there is a decrease in the number of respiratory and AOM infections in infants to whom the combination is provided.

In the present invention, the form of administration of the *Bifidobacteria* strain and the adherence-promoting probiotic is not critical, as long as a therapeutically effective amount is administered to the infant. Most conveniently, the *Bifidobacteria* strain and adherence-promoting probiotic can be supplemented into an infant formula which can then be fed to an infant.

In an embodiment, the infant formula for use in the present invention is nutritionally complete and contains suitable types and amounts of lipid, carbohydrate, protein, vitamins and minerals. The amount of lipid or fat typically can vary from about 3 to about 7 g/100 kcal. The amount of protein typically can vary from about 1 to about 5 g/100 kcal. The amount of carbohydrate typically can vary from about 8 to about 12 g/100 kcal. Protein sources can be any used in the art, e.g., nonfat milk, whey protein, casein, soy protein, hydrolyzed protein, partially hydrolyzed protein, amino acids, and the like. In one embodiment, the protein is a combination of whey protein and casein in a ratio of 60:40. Carbohydrate sources can be any used in the art, e.g., lactose, glucose, corn syrup solids, maltodextrins, sucrose, starch, rice syrup solids, and the like. Lipid sources can be any used in the art, e.g., vegetable oils such as palm oil, soybean oil, palmolein, coconut oil, medium chain triglyceride oil, high oleic sunflower oil, high oleic safflower oil, and the like.

Conveniently, commercially available infant formula can be used. For example, Enfalac, Enfamil®, Enfamil® Premature Formula, Enfamil® with Iron, Lactofree®, Nutramigen®, Pregestimil®, and ProSobee® (available from Mead Johnson & Company, Evansville, Ind., U.S.A.) may be supplemented with suitable levels of the *Bifidobacteria* strain and the adherence-promoting probiotic and used in practice of the method of the invention.

The infant formula of the present invention may contain ingredients designed to promote the growth of *Bifidobacteria* within the intestinal mucosa. For example, *Bifidobacteria* require ferrous iron, riboflavin and biotin for growth. These may be provided in combination with other ingredients in the infant formula.

As an alternative to an infant formula administration, the *Bifidobacteria* strain and the adherence-promoting probiotic can be administered as a supplement not integral to the formula feeding.

The present invention can be used to treat or prevent respiratory infections or AOM in infants that are exclusively formula-fed or in infants that are fed a combination diet of breast milk and infant formula.

In a particular embodiment of the invention, at least one prebiotic can be supplemented into the infant's diet in combination with the *Bifidobacteria* strain and adherence-promoting probiotic. In this embodiment, the prebiotic can be any prebiotic known in the art. In a particular embodiment, the prebiotic is selected from the group consisting of galacto-oligosaccharide, inulin, fructo-oligosaccharide, lactulose, neosugars, and combinations thereof.

In an embodiment of the present invention, the *Bifidobacteria* strain and the adherence-promoting probiotic are supplemented into the diet of the infant from birth until the infant reaches about one year of age. In another embodiment of the present invention, the *Bifidobacteria* strain and the adherence-promoting probiotic are supplemented into the diet of the infant from birth until the infant reaches about three years of age.

In an embodiment, a therapeutically effective amount of the *Bifidobacteria* strain and the adherence-promoting probiotic is between about $10^5$ and $10^{11}$ colony forming units (cfu). In another embodiment, a therapeutically effective amount of the *Bifidobacteria* strain and the adherence-promoting probiotic is between about $10^6$ and $10^8$ cfu. In an embodiment, the therapeutically effective amount is administered daily. In other embodiments, the therapeutically effective amount can be administered every other day, weekly or monthly. The frequency and size of the probiotic dose will depend, for example, upon the microorganism chosen, the delivery vehicle and the infant to whom the dose is administered.

It is well within the level of knowledge of one of skill in the art to provide increased dosages, as determined by those of skill in the art to be safe and effective for an individual infant. Furthermore, minimum amounts may be varied based upon their combination with prebiotic compositions and other additives that may enhance the colonization of the *Bifidobacteria* strain.

In an embodiment of the present invention, the ratio of Bb-12 to LGG can be between about 10:1 and 1:10. In another embodiment of the invention, the ratio of Bb-12 to LGG can be between 5:1 and 1:5. In yet another embodiment of the invention, the ratio of Bb-12 to LGG can be between about 3:1 and 1:3. In a particular embodiment of the invention, the ratio of Bb-12 to LGG can be about 1:1.

The probiotic organisms of the present invention can be provided as a powder, in capsular form, as a component of an emulsion or a paste, or in any other suitable carrier determined by those of skill in the art to be an effective carrier for live microorganisms. Powder compositions containing probiotic microorganisms can be provided in individual pouches, for example, for admixing with infant formula or early foods. Capsules, for example, may be opened so that the contents can be mixed with infant formula, strained foods, milk, juice, or other foods for providing a nutritional composition to an infant. An emulsion or paste can also be admixed into a variety of foods.

In an embodiment, the supplementation of a *Bifidobacteria* strain and an adherence-promoting probiotic prevents or treats the occurrence of upper respiratory infection, influenza, croup, respiratory syncytial virus, bronchitis, bronchiolitis and/or pneumonia. In another embodiment, the supplementation of a *Bifidobacteria* strain and an adherence-promoting probiotic prevents or treats the occurrence of AOM.

Figure 2:
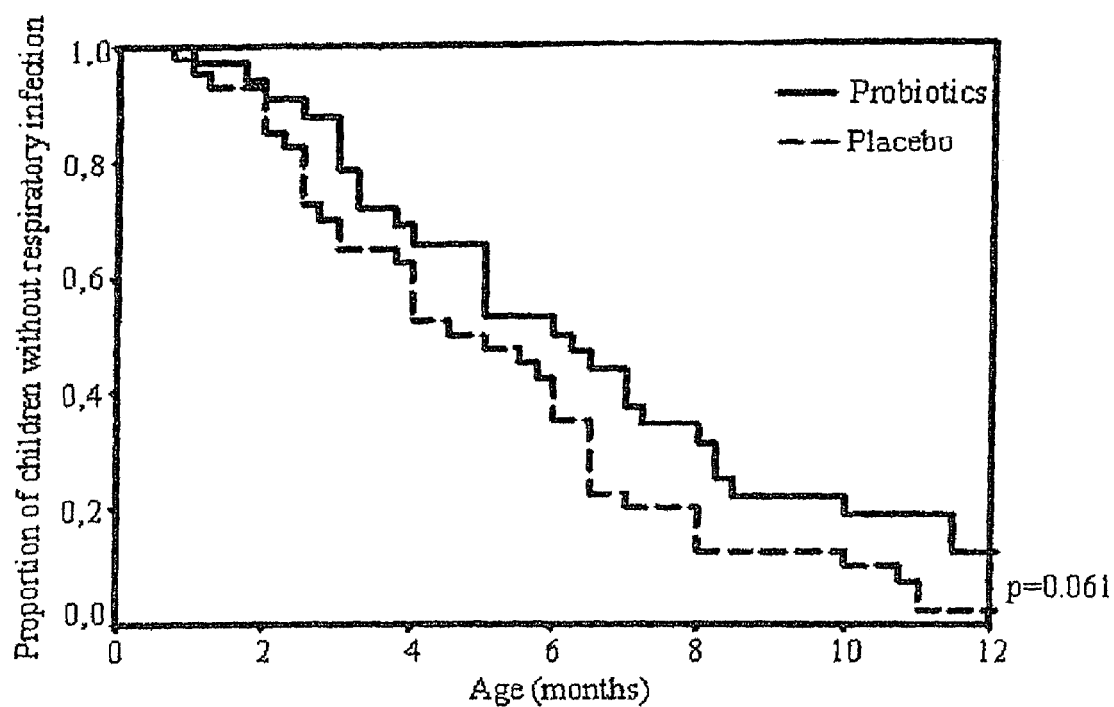
FIG. 2 is a graph indicating the effect of probiotic supplementation on the development of a respiratory infection during the first year of life.

A significant reduction in the incidence of early and recurrent infections and the use of antibiotics during the first year of life was achieved by the particular probiotic combination of the present invention. The effect was most prominent with regard to respiratory infections and AOM, the most prevalent infection in infancy. This is shown in FIGS. 1 and 2. These figures illustrate that probiotic supplementation reduced the proportion of children that develop a respiratory infection or AOM episode during the first year of life. The present invention was also effective in reducing the occurrence of recurrent respiratory infections and recurrent AOM infections. Moreover, probiotics appeared to confer protection against early infections, the importance of which culminates in the fact that the children developing frequent infections, including AOM, experience their first infection early.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

Example 1

This example describes the materials and methods necessary to show the effect of a strain of *Bifidobacteria* and an adherence-promoting probiotic on the frequency of respiratory infections and AOM.

The infants participating in the double-blind, placebo-controlled clinical study conducted by the inventors were recruited in well-baby clinics in Turku, Finland between September 2000 and May 2002. The sole inclusion criterion for the study was the need for infant formula before the age of two months. Infants with chronic disease were excluded.

In total, 81 infants were block-randomized with individual codes to receive either $1 \times 10^{10}$ colony-forming units of both *Bifidobacterium lactis* Bb-12 and LGG or a microcrystalline cellulose placebo daily until the age of 12 months. The daily probiotics or placebo were provided in visually identical capsules, the contents of which were supplemented into infant formula (Enfamil®, Mead Johnson Nutritionals, Evansville, Ind.). The formula was to be used as the sole infant formula during this period. Maternal use of commercially available products containing probiotics was discouraged.

Clinical examination of the infants was performed at scheduled visits at the ages of 3, 7, and 12 months. The follow-up was completed by 72 of the 81 (89%) infants enrolled. The mean age at the time of withdrawal amongst the 9 infants who did not complete the follow-up was 2.9 months (range 1.5 to 7.0) and, therefore, only the infants who completed the study were included in the analysis.

To ascertain that the probiotics remained viable during storage, microbiological analysis of a random sample of capsules was performed by microbiologist in a blinded fashion. Viable counts between $1 \times 10^9$ and $1 \times 10^{10}$ per capsule were found for both LGG and Bb-12.

All infections during the study period were recorded in special diaries by the family or the family physician. Respiratory infections, doctor-diagnosed AOM, gastrointestinal infections, and the number of treatments with antibiotic agents were separately recorded in detail. The primary outcome measure for the study was the incidence of early respiratory infections, doctor-diagnosed AOM, and gastrointestinal infections. The incidence of recurrent (defined as 3 or more occurrences) infections during the first year of life were considered secondary outcome measures. Early or recurrent need for antibiotics were interpreted to reflect suspected early or recurrent bacterial infections, respectively, and thus recorded. Tympanostomy before the age of 12 months was interpreted to indicate frequent ear infections. Tympanostomy is a surgical procedure that requires general anesthesia, but may be necessary to avoid structural damage to the ear which may occur as the result of AOM.

All health problems in the study population during the first year of life were recorded in detail to distinguish between symptoms of diseases with infectious and non-infectious etiology. Gastro-esophageal reflux disease as a possible noninfectious cause of cough, vomiting, or increased fussing was confirmed or excluded using a 24-hour esophageal pH probe study. The diagnosis of cow's milk allergy, a non-infectious cause of gastrointestinal or cutaneous symptoms, was confirmed by a double-blind, placebo controlled cow's milk challenge. Atopic eczema was diagnosed using the criteria introduced by Hanifin. Hanifin, J. M., *Atopic Dermatitis in Infants and Children*, Pediatr. Clin. Nutr. Am. 38:763-89 (1991). Atopic sensitization was assessed by skin prick testing at the ages of 7 and 12 months. The tested antigens included banana, potato, carrot, apple, wheat, rice, milk, egg, cod, soybean, and gliadin. The infant was considered sensitized in case of one or more positive reactions at either time point.

To ascertain compliance with the intervention, fecal samples were collected at enrollment prior to probiotic supplementation and again at the age of 3 months and stored at −86° C. Samples were available from 46 infants at enrollment and 45 infants at the age of 3 months. The fecal samples were thawed and serially diluted in phosphate buffered saline (pH 7.2, 10 mM phosphate). For the detection of LGG, dilutions were spread on Rogosa agar (Oxoid, Basingstoke, UK) and incubated aerobically at 37° C. for four days. Typical LGG colonies were purified and DNA was extracted from the colonies. Strain identity was verified by polymerase chain reaction.

The data were expressed as means with range or medians with IQR to give an estimate of the distribution of the data. The comparisons between the groups at baseline were conducted using the Mann-Whitney U test and the $X^2$ test. Logistic regression analysis was used to compare the treatment groups with respect to early infections and recurrent infections and recurrent need for antibiotic treatment during the first 12 months of life. The analyses of recurrent infections and antibiotic treatment were performed with and without adjustment for other relevant factors. Stepwise regression analyses were performed in a forward manner in order to control for the relevant risk factors or confounding factors. The treatment group was forced to the model and the other factors introduced to the model were: gender, mode of birth, duration of exclusive breastfeeding, total duration of breastfeeding, older siblings, maternal smoking, pet ownership and family history of allergy. The criteria for entering and removing a variable were: probability of F-to-enter $\leq 0.10$ and F-to-remove $\geq 0.15$. The results are given in terms of relative risk, also known as risk ratio (RR), and 95% confidence interval (CI). Kaplan-Meier curves were applied for the time without a respiratory infection and time without an AOM and log rank test was used to compare the treatment groups. The data were analyzed using the SPSS (Version 11.5).

Example 2

This example illustrates the effects of Bb-12 and LGG on the frequency of respiratory infections and AOM. The baseline characteristics, shown in Table 1, were similar in infants receiving probiotics and placebo.

TABLE 1

| Baseline Characteristics and History | | |
|---|---|---|
| | Probiotics (n = 32) | Placebo (n = 40) |
| Boys | 16 (50%) | 19 (48%) |
| Gestational age mean (range) | 39.8 weeks (36.7 to 42.1) | 39.9 weeks (35.1 to 42.3) |
| Birthweight mean (range) | 3440 g (2300 to 4100) | 3540 g (2140 to 4580) |
| Older siblings | 15 (47%) | 24 (60%) |
| Parental smoking | 18 (56%) | 22 (55%) |
| Exclusive breastfeeding mean (range) | 1.9 weeks (0.0 to 6.0) | 1.9 weeks (0.0 to 6.0) |
| Total breastfeeding mean (range) | 2.0 months (0.25 to 12.0) | 2.4 months (0.25 to 7.5) |
| Age at start of intervention (range) | 38 days (6 to 65) | 35 days (2 to 59) |

The mean age at start of intervention was 38 days (range 6-65) 5 in infants receiving probiotics and 35 days in (range 2-59) in infants receiving placebo. The follow-up was completed by 72 of the 81 (89%) infants enrolled. The mean age at the time of withdrawal amongst the 9 infants who did not complete the follow-up was 2.9 months (range 1.5-7.0) and therefore only the infants who completed the study were included in 10 the analysis.

The study probiotics reduced the risk of early respiratory infections and AOM as well as the need for antibiotic treatment during the first 7 months of life. These results are presented in detail in Table 2.

TABLE 2

The Incidence of Infections during the First 7 Months of Life

|  | Probiotics (n = 32) | Placebo (n = 40) | RR (95% CI) | Adjusted RR (95% CI) |
|---|---|---|---|---|
| Respiratory Infection | 22 (69%) | 31 (78%) | 0.85 (0.44 to 1.19) | 0.85 (0.44 to 1.19) |
| AOM | 7 (22%) | 20 (50%) | 0.34 (0.10 to 0.90) | 0.31* (0.09 to 0.85) |
| Gastrointestinal Infection | 1 (3%) | 6 (15%) | 0.19 (0.003 to 1.64) | 0.19 (0.003 to 1.64) |
| Antibiotic Use | 10 (31%) | 24 (60%) | 0.39 (0.14 to 0.92) | 0.36† (0.11 to 0.91) |

*Adjusted for maternal allergies
†Adjusted for maternal allergies and mode of birth During the first 7 months of life, 25/32 (78%) of infants receiving probiotics and 36/40 (90%) of infants receiving placebo had encountered at least one episode of acute infection. Specifically, 7/32 (22%) infants receiving probiotics and 20/40 (50%) of infants receiving placebo experienced AOM. Antibiotics were prescribed for 10/32 (31%) of infants receiving probiotics and 24/40 (60%) of infants receiving placebo. During the first 7 months of life, 22/32 (69%) of infants receiving probiotics and 31/40 (78%) of infants receiving placebo had encountered at least one episode of respiratory infection. Thus, probiotic supplementation decreased the risk for early AOM, respiratory infection and antibiotic use. The incidence of gastrointestinal infections during the first 7 months of life was low in both groups.

In addition to effects during the first 7 months of life, probiotics reduced significantly the incidence of recurrent infections during the first 12 months of life. These results are shown in Table 3.

TABLE 3

The Incidence of Recurrent Infections and Use of Medical Interventions during the First 12 Months of Life

|  | Probiotics (n = 32) | Placebo (n = 40) | RR (95% CI) | Adjusted RR (95% CI) |
|---|---|---|---|---|
| Any Infection | 22 (69%) | 31 (78%) | 0.22 (0.05-0.98) | 0.47 (0.16 to 1.20) |
| Respiratory Infection | 9 (28%) | 22 (55%) | 0.40 (0.14 to 0.97) | 0.48‡ (0.16 to 1.20) |
| AOM | 4 (13%) | 10 (25%) | 0.47 (0.10 to 1.58) | 0.54§ (0.11 to 1.88) |
| Antibiotic Use | 10 (31%) | 16 (40%) | 0.76 (0.30 to 1.53) | 0.71** (0.20 to 1.74) |
| Tympanostomy | 0 (0%) | 4 (10%) | 0.23 (N/A to 1.91) | 0.23 (N/A to 1.91) |

‡Adjusted for older siblings and paternal allergy
§Adjusted for older siblings
**Adjusted for older siblings, maternal smoking, pet ownership, duration of exclusive breastfeeding and maternal allergy During the first 12 months of life, a total of 53/72 (74%) of infants participating in the study experienced 3 or more infections. More specifically, 31/72 (43%) of infants suffered from recurrent respiratory infections and 14/72 (19%) from recurrent AOM during this period. Moreover, 26/72 (36%) of infants experienced a recurrent need for antibiotic treatment. Probiotics significantly reduced the incidence of recurrent respiratory infections during the first 12 months of life.

For example, 9/32 (28%) infants receiving probiotics and 22/40 (55%) of infants receiving placebo experienced three or more respiratory infections. Of the infant receiving probiotics, only 4/32 (13%) experienced three or more incidences of AOM. In contrast, of those infants receiving placebo, 10/40 (25%) experienced three or more incidences of AOM. In addition, the administration of probiotics tended to reduce the need for tympanostomy, performed either to prevent recurrent AOM or to treat secretory otitis media. None of the infants receiving probiotics required tympanostomy during the first year of life, whereas the procedure was performed on 4/40 (10%) of the infants receiving placebo.

Several factors were associated with the risk of recurrent infections and recurrent need for antibiotic treatment. Having older siblings increased the risk for recurrent respiratory infections, the recurrent need for antibiotics, and tended to increase the risk for recurrent AOM during the first 12 months of life. A family history of allergy increased the risk for recurrent infections and maternal smoking was associated with recurrent antibiotic use. The duration of exclusive breastfeeding had an inverse association with recurrent antibiotic use. Pet ownership conferred protection against recurrent infections and recurrent need for antibiotics. Consequently, the effect of probiotic supplementation on the risk of recurrent infections during the first 12 months of life was adjusted for these factors.

Gastro-esophageal reflux disease was diagnosed in 1/32 (3%) infants receiving probiotics and 3/40 (8%) infants receiving placebo. None of the 32 infants receiving probiotics had cow's milk allergy as compared to 3/40 (8%) infants receiving placebo. In all, 4/32 (13%) infants receiving probiotics and 8/40 (20%) infants receiving placebo suffered from atopic eczema during the first year of life. Atopic sensitization was detected in 2/32 (6%) infants receiving probiotics and 3/40 (8%) infants receiving placebo. None of the probiotic-supplemented infants in the study experienced more than 2 gastrointestinal infections during the study period.

The relationship between fecal recovery of LGG at 3 months of age and the risk of infection during the first 7 months of life was also evaluated. These results are presented in Table 4.

TABLE 4

The Relationship of Fecal Recovery of LGG at 3 Months of Age and the Risk of Infections During the First 7 Months of Life

|  | Positive (n = 23) | Negative (n = 22) | RR (95% CI) |
|---|---|---|---|
| Respiratory Infection | 15 (65%) | 18 (82%) | 0.68 (0.19 to 1.21) p = 0.31 |
| AOM | 4 (17%) | 10 (45%) | 0.30 (0.06 to 1.13) p = 0.057 |
| Antibiotic Use | 7 (30%) | 12 (55%) | 0.46 (0.12 to 1.27) p = 0.14 |
| Recurrent Respiratory Infections | 1 (4%) | 2 (9%) | 0.47 (0.01 to 6.95) p = 0.61 |
| Recurrent AOM | 0 (0%) | 2 (9%) | 0.38 (N/A to 5.05) p = 0.23 |
| Recurrent Antibiotic Use | 0 (0%) | 5 (23%) | 0.12 (N/A to 0.94) p = 0.022 |

Prior to probiotic supplementation, LGG was recovered in the feces of 12/46 infants, 8/28 (29%) in the probiotics group and 4/18 (22%) in the placebo group. Pre-intervention presence of LGG in feces was not associated with the incidence of infections in general, respiratory infections, AOM or gastrointestinal infections, nor was there an impact on antibiotic use at any age. At 3 months of age, i.e. after a minimum of 1 month of probiotic supplementation, LGG was recovered in 21/28 (75%) of infants receiving probiotics and 2/17 (12%) of infants receiving placebo, p<0.0001. Furthermore, the presence of LGG in feces at this time was associated with a reduced risk of having encountered at least one episode of AOM by the age of 7 months; 4/23 (17%) and 10/22 (45%) infants positive and negative for LGG, respectively. The presence of LGG in feces at 3 months of age was also indicative of protection against recurrent infections: 2/23 (9%) and 10/22 (45%) in infants positive and negative for LGG, respectfully, and recurrent need for antibiotics: 0/23 (0%) and 5/22 (23%) in infants positive and negative for LGG, respectively, by the age of 7 months.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for reducing the incidence of respiratory infections in an infant between the ages of birth and about one year, the method comprising the steps of:
   administering to the infant *Bifidobacteria lactis* Bb-12 incorporated into an infant formula; and
   administering *Lactobacillus rhamnosus* GG with the *Bifidobacteria lactis* Bb-12, wherein the ratio of *Bifidobacteria lactis* Bb-12 to *Lactobacillus rhamnosus* GG is between about 10:1 and 1:10 and wherein the infant formula provides about $10^5$ to about $10^{11}$ cfu/day to the infant.

2. The method according to claim 1, further comprising the administration of at least one prebiotic.

3. The method according to claim 2, wherein the prebiotic is selected from the group consisting of galacto-oligosaccharide, inulin, fructo-oligosaccharide, lactulose, neosugars, and combinations thereof.

4. A method for reducing the incidence of acute otitis media in an infant, the method comprising administering to the infant from birth until about one year of age *Bifidobacteria lactis* Bb-12, together with *Lactobacillus rhamnosus* GG, wherein the *Bifidobacterium lactis* Bb-12 and the *Lactobacillus rhamnosus* GG are administered together in an infant formula in a ratio of between about 10:1 and 1:10 and in an amount sufficient to provide between about $10^5$ and $10^{11}$ cfu/day.

5. The method according to claim 4, wherein the amount of *Bifidobacterium lactis* Bb-12 and *Lactobacillus rhamnosus* GG administered is between about $10^6$ and $10^8$ cfu/day.

6. The method according to claim 1, wherein the ratio of *Bifidobacterium lactis* Bb-12 and *Lactobacillus rhamnosus* GG is between about 5:1 and 1:5.

7. The method according to claim 1, wherein the ratio of *Bifidobacterium lactis* Bb-12 and *Lactobacillus rhamnosus* GG is about 1:1.

8. The method according to claim 4, wherein the ratio of *Bifidobacterium lactis* Bb-12 and *Lactobacillus rhamnosus* GG is between about 5:1 and 1:5.

9. The method according to claim 4, wherein the ratio of *Bifidobacterium lactis* Bb-12 and *Lactobacillus rhamnosus* GG is about 1:1.

10. The method according to claim 4, further comprising the administration of at least one prebiotic.

11. The method according to claim 10, wherein the prebiotic is selected from the group consisting of galacto-oligosaccharide, inulin, fructo-oligosaccharide, lactulose, neosugars, and combinations thereof.

* * * * *